United States Patent [19]

Guy et al.

[11] Patent Number: 4,473,646

[45] Date of Patent: Sep. 25, 1984

[54] STEREOSPECIFIC ASPARAGINASES

[75] Inventors: Graeme R. Guy, South Australia, Australia; Hugh W. Morgan; Roy M. Daniel, both of Hamilton, New Zealand

[73] Assignee: Development Finance Corp. of New Zealand, Wellington, New Zealand

[21] Appl. No.: 253,112

[22] Filed: Apr. 10, 1981

[30] Foreign Application Priority Data

Apr. 21, 1980 [NZ] New Zealand .................. 193493

[51] Int. Cl.$^3$ .................. C12N 9/82; C12N 1/20
[52] U.S. Cl. .................. 435/229; 435/815; 435/253
[58] Field of Search .................. 435/229, 109, 68, 814, 435/815, 253; 424/94

[56] References Cited

U.S. PATENT DOCUMENTS

| | | | |
|---|---|---|---|
| 3,589,982 | 6/1971 | Peterson et al. | 435/229 |
| 3,652,402 | 3/1972 | Chibata et al. | 435/814 |
| 3,664,926 | 5/1972 | Grabner et al. | 435/229 |
| 3,669,842 | 6/1972 | Tanaka et al. | 435/815 |
| 3,713,983 | 1/1973 | Yokotsuka et al. | 435/219 |
| 3,953,296 | 4/1976 | Trutnousky et al. | 435/14 |

OTHER PUBLICATIONS

Hickey et al., The Electron Transport System of an Extremely Thermophlic Bacterium, *J. of Gen. Micro.*, 1979, 114, pp. 195–200.

Degryse, et al., A Comparative Analysis of Extreme Thermophilic Bacteria Belonging to the Genus Thermus *Chem. Abs.* vol. 89, 1978, p. 420.

Brock, et al., Thermus aquaticus gen. n. and sp. n., a Non-sporulating Extreme Thermophilie, *J. of Bacteriology*, vol. 98, No. 1, pp. 289–297 1969.

Watanabe, et al., Thermophilic L-asparginase *Chem Abstracts* vol. 86, 1977 p. 424.

"The Purification and Some Properties of a Stereospecific D-Asparaginase from an Extremely Thermophilic Bacterium, Thermus aquaticus" Graeme R. Guy and R. M. Daniel; 1982.

"Stereospecific Asparginases in Smooth Brucella abortus, Strain 19" Robert A. Altenbern and Riley D. Housewright, Aug. 21, 1953.

"Geology of Whakarewarewa Hot Springs:, E. F. Lloyd, 1975.

*Primary Examiner*—Albert T. Meyers
*Assistant Examiner*—Kathleen S. McCowin
*Attorney, Agent, or Firm*—Murray, Whisenhunt and Ferguson

[57] ABSTRACT

There is described a method of separating an asparaginase rich fraction from a thermophilic microoganism and then to divide this fraction into its D- and L-asparaginases. Substantially pure crystals of the D-asparaginase were obtained.

16 Claims, No Drawings

Flow diagram of THERMUS T-351 asparaginase purification
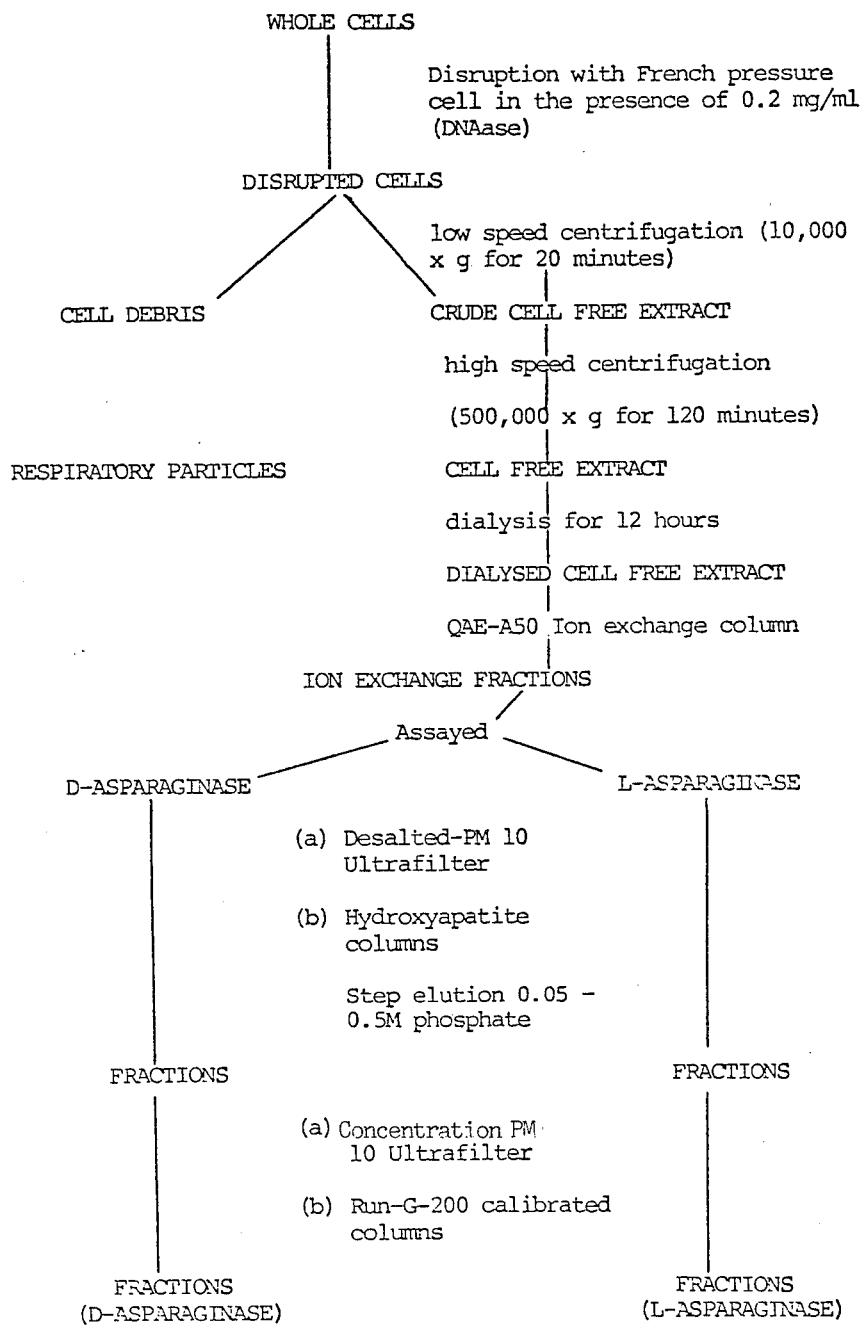

Flow diagram of THERMUS T-351 asparaginase purification
(Continued)
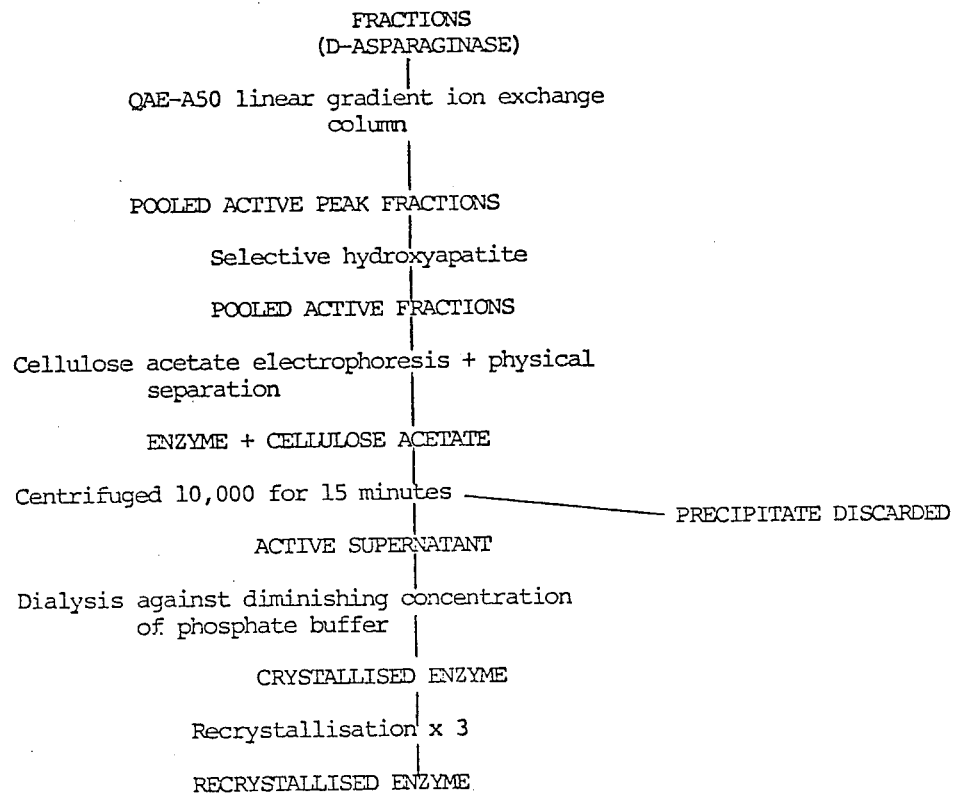

STEREOSPECIFIC ASPARAGINASES

CROSS-REFERENCES TO RELATED APPLICATIONS

The thermophilic micro-organism from which the asparaginases of this invention are derived are described and claimed in co-pending application U.S. Ser. No. 176,528 filed on Aug. 8, 1980 now U.S. Pat. No. 4,442,214. A protease derived from the same micro-organism is described and claimed in co-pending application U.S. Ser. No. 176,527 filed on Aug. 8, 1980.

BACKGROUND OF THE INVENTION

1. Field of the Invention

This invention relates to asparaginase enzymes having stereospecificy.

2. Description of the Prior Art

Asparaginases are known to be useful in chemotherapy, in optical isomeric formation and preparation and as fine biochemicals. It is desirable to have asparaginases which exhibit a strong stereospecificity.

It is an object of the invention to go some way towards achieving this desideratum or at least to offer the public a useful choice.

SUMMARY OF THE INVENTION

Accordingly the invention may be said broadly to consist in a D-asparaginase having the properties set out in the centre column of Table 1 herein.

In another aspect the invention may be said broadly to consist in an L-asparaginase having the properties set out in the left hand column of Table 1 herein.

Preferably said D-asparaginase is derived from (VARIETY T-351) having an ATCC deposit number of 31,674, hereinafter referred to as THERMUS T-351, ATCC No. 31,674.

Preferably said L-asparaginase is derived from THERMUS T-351, ATCC No. 31,674.

In another aspect the invention may be said broadly to consist in a process for deriving and separating D-asparaginase and L-asparaginase which comprises taking whole cells of THERMUS T-351, ATCC No. 31,674 subjecting said whole cells to a cell disrupting process and separating an asparaginase-rich fraction from the cell debris in the mixture formed by said disrupting process, concentrating and purifying said asparaginase-rich fraction and separating D-asparaginase from L-asparaginase in said asparaginase-rich fraction.

Preferably said D-asparaginase is subjected to further purification steps.

Preferably said L-asparaginase from which said D-asparaginase has been separated is subjected to further purification steps.

Preferably said cell disrupting process comprises a process selected from the group consisting of pressure disruption and sonication.

Preferably said asparaginase rich fraction is separated from said cell debris by centrifugation.

Preferably said centrifugation comprises a first low speed centrifugation followed by a second high speed centrifugation of the supernatant from the low speed centrifugation.

Preferably said concentration and purification steps comprise a series of dialyses and ion exchange processes.

Preferably said further purification steps comprise ultrafiltration and ion exchange.

Preferably the final purification step comprises recrystallisation.

DESCRIPTION OF THE PREFERRED EMBODIMENTS

THERMUS T-351 is a micro-organism isolated from Hot Pool No. 351 as marked on the map of "Whakarewarewa Hot Srings", 1:2000, 1st Edition by New Zealand Geological Survey (Bibliographic reference—Lloyd, E. F. 1074, Geology of Whakarewarewa hot springs, DSIR information series No. 104 DSIR, Wellington, N.Z.). It is an aerobic non-spore forming gram-negative rod-shaped and caldo-active bacterium. It is similar to *Thermus aquatics* (Brock et al., *J. Bacteriol* 98, 289–287; Degryse et al, *Archives of Microbiology* 117, 18) but there exists a significant difference in cytochrome composition of between THERMUS T-351 and *Thermus aquaticus*. THERMUS T-351 exhibits optimal activity at 70° to 80° C. and negligible activity below 40° C. Other properties of this micro-organism are discussed by Hickey and Daniel in *Journal of General Microbiology* (1979), 114, 195–200. A culture sample of this micro-organism has been deposited in the American Type Culture Collection at 12,301 Parklawn Drive, Rockville, Md., U.S.A. 20852, U.S.A. under ATCC No. 31,674.

A culture of the micro-organism THERMUS T-351 is subjected to a centrifugation step as described in the aforementioned U.S. Ser. No. 176,528 to remove the protease excreted by the whole cells as the supernatant. The whole cells are then recovered and subjected to the process as set out in the flow diagram appearing in the drawings and more expressly described in Examples 1 and 2.

EXAMPLE 1

Method of Isolation and Separation of Asparaginases

A. Preparation of cell free extracts 120 gm cell cakes of whole cells of THERMUS T-351, stored in liquid nitrogen, were thawed and made to a moderately thich suspension with TRIS/HCl buffer 0.5 M (pH 8.2), plus 0.22 M NaCl, and 0.2 mg per ml of DNAase (Sigma), using a motorised tissue-grinder. The whole cells were then disrupted by three passages through a French Pressure Cell (Aminco, Silver Springs, Maryland), at 60,000 kPa. Cell debris and unbroken cells were removed by centrifugation at $10,000 \times g$ for 20 minutes. The cell debris obtained from the low speed centrifugation was reprocessed through the French pressure cell and the rest of the centrifugation processes. The supernatant was carefully removed with a pipette and sealed in 10 ml tubes for centrifugation in a MSE 75 Superspeed ultracentrifuge for 2 hours at $500,000 \times g$. The upper ⅔ of the high speed supernatant was carefully removed from each tube and bulked prior to being dialysed overnight in 1 cm dialysis tubing against TRIS/HCl buffer 0.05 M and pH 8.2.

B. Ion Exchange Chromatography

The dialysed fraction was loaded onto a QAE-A50 Sephadex column ($15 \times 2.5$ cm) (Pharmacia Fine Chemicals) equilibrated with TRIS/HCl (0.5 M, pH 8.2) buffer. The sample was washed onto the column with approximately 100 mls of the equilibrating buffer. All steps were pumped through the column with a Pharmacia Peristalitic pump (P-3) at a rate of 1–2 ml min$^{-1}$.

Step gradients of NaCl 0.05, 0.10, 0.15, 0.20, 0.30, 0.40, and 0.50 Molar in the same buffer were applied to the column, the application of each successive concentration being made after the return to baseline of the recorder. The eluate was monitored at 220 nm through a 1 cm pathlength flow cell in a Cecil 272 spectrophotometer recording on an Omniscribe chart recorded and 80 drop fractions collected in tubes on an L.K.B. "Ultrorac" (Model 7000) fraction collector.

This step results in the separation of D-asparaginase from L-asparaginase. All subsequent steps involving L-asparaginase were carried out in the presence of 1 mM mercaptrethanol to stabilise the enzyme.

Both enzymes are then further purified as indicated below.

EXAMPLE 2

Purification of D-asparaginase and L-asparaginase

A. Hydroxyapatite ion exchange/adsorption chromatography

Ion exchange step C for Example 1 separated the two stereospecific asparaginases. They were then each individually desalted using a PM 10 ultrafilter (Amicon) in a Chem-Lab Ultrafiltration cell (model C 50), at room temperature.

The eluates were loaded onto separate hydroxyapatite (Biorad Bio-Gel HTP) columns 2.5×15 cm, which had been loaded according to manufacturer's instructions and equilibrated with 100 ml of distilled water which followed a complete reverse run of the phosphate step gradient to be used. (All solutions were passed through the columns with a head height of 1.5 meters). The columns were then eluted with phosphate buffer concentrations consisting of the following molarities; 0.005, 0.01, 0.02, 0.04, 0.08, 0.2 and 0.5, all at pH 6.9.

B. Gel Exclusion Chromatography

Fractions from the two hydroxyapatite columns were individually assayed, pooled, desalted, washed and concentrated using a PM 10 ultrafilter. Concentration of asparaginase containing fractions took the volume down to 7–10 mls which were then frozen in liquid nitrogen and freeze dried. They were later reconstituted with 2.0 ml of TRIS/HCl buffer pH 8.2, and each was run separately on a Sephadex G-200 (Pharmacia Fine Chemicals) column 2.5×65 cm. The columns had been packed using downflow eulution according to manufacturers instructions. Standards used to calibrate the columns were; Blue dextran (MW $2\times10^6$), catalase (MW $2.48\times10^5$), gamma globulin (MW $1.69\times10^4$), lipoxidase (MW $9.74\times10^4$), ovalbumin (MW $4.35\times10^4$), α-chymotrypsin (MW $2.37\times10^4$) and cytochrome C (horse heart) (MW $1.3\times10^4$). 5.0 mg of each of these standards were applied in 2.0 ml of elution buffer.

EXAMPLE 3

Further Purification of D-asparaginase

A. Ion Exchange/Linear Gradient Column

The step following the gel exclusion chrometography consisted of application of pooled active fractions to a 10×2.5 cm QAE-A50 Sephadex column which was eluted with a linear NaCl gradient from 0.1 M to 0.2 M this time at a pH of 7.0.

B. Selective Hydroxyapatite Chromatography

This method of extraction used the same hydroxyapatite column as before. The method relies on a conformational change induced specifically in the asparaginase enzymes by adding one of the products of the enzymic reaction, in this case, ammonia. This is added to 0.05 M and 0.2 M phosphate buffers which is the range of the applied linear gradient.

0.1 mM of $(NH_4)_2SO_4$ was added to a total of 500 ml of phosphate buffer at a pH of 7.2, and the column run as already described.

C. Cellulose Acetate Electrophoresis

Cellulose acetate electrophoresis was used both as an indication of purity and as a preparative technique. Titan III cellulose acetate plates were soaked in Helena HR buffer, pH 8.0 and after blotting dry were imprinted in the plate center with a perspex sample applicator. Samples of enzyme solution, 2–10 μL, were applied into the depressions thus made. The plates were run at 450 V and 6 mA for 60 minutes after which they were stained for 4 minutes in Ponceau S solution followed by destaining for 30 minutes, with several changes, in 5% acetic acid solution. The same system was run at pH 6.5 and 4.5 to determine homogeneity of the protein band.

The penultimate separation step revealed two distinct bands using the above system and a derivation of it was used to achieve final purity.

A continuous depression was made across the centre of a 2×2 inch plate, excluding about 5 mm at both edges. The concentrated enzyme sample (made by adding 200 μL of buffer to freeze dried enzyme) was added to the centre depression of four such plates. There were run for 60 minutes after which edge segments were cut from both sides of each plate and stained to locate the two protein bands. After careful measuring, parallel segments of 0.5–0.75 mm were cut with a razor blade across the protein containing regions. A preliminary incubation of 0.04 M asparagine with the cellulose acetate stripped from the plastic backing and macerated in 200 μL of TRIS/HCl buffer was followed by spotting each sample on Whatman No. 1 chromatography paper. Development of the descending chromatograms was by phenol:water (80:20) followed by spraying with ninhydrin, which revealed the location of the active enzyme by the appearance of aspartic acid, the reaction product. The cellulose strips containing active enzyme were pooled, stripped and macerated overnight in the TRIS/HCl buffer.

D. Crystallisation

The enzyme containing fraction from the above step was centrifuged at 10,000×g for 10 minutes to remove insoluble cellulose particles in the pelleted precipitate. The supernatant was carefully placed in 5 mm dialysis tubing and dialysed for 24 hours with progressively lowering concentrations of TRIS/HCl buffer until dialysing finally against distilled water. The solution was removed from the dialysis tubing, placed in a microbeaker and ethanol was added dropwise with constant mixing until incipient cloudiness (approximately ⅛ volume of ethanol). The mixture was kept at 4° C. overnight during which time crystals formed. The crystals were washed in 50% ethanol and dissolved in distilled water. Ethanol was added dropwise at room temperature with constant mixing until incipient cloudiness again formed. The solution was clarified by centrifugation at 10,000×g for 15 minutes. Crystals appeared in the supernatant after standing at room temperature overnight. The crystals were separated from the solution by centrifugation, washed several times with 50% ethanol and dried in a vacuum. Recrystallisation was repeated three times. The whole process was repeated from the cellulose acetate stage with no included protein, as a control. No crystals were obtained from the control procedure whereas the D-asparaginase crystals showed good activity when dissolved in minimal amounts of buffer.

Observed properties of the asparaginase enzymes according to this invention and comparative properties from L-asparaginase derived from *E. coli* (B) are set out in Table 1.

brilliant blue, destained by continuous stirring with several changes of methanol: acetic acid: water solution (20:1:20). The D-asparaginase enzyme solutions (purified) were concentrated fourfold with a PM 10 ultrafilter prior to being incubated with 1% SDS solution overnight at 37° C.

Mobility ($R_f$) was calculated as:

TABLE 1
Summary of Asparaginase properties

| Property | L-asparaginase THERMUS T-351 | D-asparaginase THERMUS T-351 | L-asparaginase *E. COLI* (B) (for comparison) |
|---|---|---|---|
| Molecular Weight | 80,000 | 62,000 | 141,000 |
| Subunits | | | |
| number | 4 | 2 | 2 |
| molecular weight | 20,000 | 30,000 | 70,000 & 35,000 |
| Isoelectric point | 4.6 | 4.8 | 4.75 |
| pH optimum | 9.5 | 9.5 | 7.5 |
| Sulphydryl enzyme | Yes* | No | No |
| Specificity | only for L-asparagine | Only for D-asparagine | L-asparagine 100 D-asparagine 5 L-glutamine 9 D-glutamine 0.92 |
| $K_m$ | — | $20 \times 10^{-3}$ M | $4 \times 10^{-5}$ M |
| Inhibitors: | | | |
| Increasing ionic Strength | Loses activity with increasing concentrations (47% loss at 0.1 M NaCl) | Loses activity with increasing concentrations Similar to L-asparagine) | Only loses activity at high concentrations (4 M) |
| pCMB | 100% loss of activity | No loss of activity | No loss of activity |
| Acetamide | No loss of activity | 100% loss of activity | No loss of activity |
| Other | — | D & L serine D & L histidine α-ketoacids | — |
| Enzyme location | Cytoplasmic | Periplasmic region | Cytoplasmic |
| Resistance to Proteolysis: | | | |
| Trypsin 50 mg ml$^{-1}$ Chymotrypsin 50 mg ml$^{-1}$ Caldolysin 29 mg ml$^{-1}$ | — | Loses 0–1% of original activity only after 30 minutes incubation, in each case | Loses 95–199% of activity after 10 minutes, in each case |
| Cold sensitivity (25 μg ml$^{-1}$ at enzyme) 0–4° C. | loses activity irreversibly after 12 hours | Completely stable: i.e. no activity loss after 30 days | Irreversible loss (100%) after 4 days |
| Longevity: | | | |
| Activity loss after: 2 hours at 75° 12 hours 24 hours | 8% 10% 12% | 7% 9% 13% | 100% 100% 100% |
| Amino acids found in active site | — | Histidine + No [lysine, tyrosine, serine] | valine, glycine, alanine, methionine, arginine, proline, serine, threonine |

*6 disulphide bonds

EXAMPLE 4
Methods of Checking Purity

A. Disc Electrophoresis

Sodium dodecyl sulphate (SDS) polyacrylamide gel electrophoresis was performed by the method of Weber and Osborn [(1969) *J. Biol, Chem.* 244, 4406–4412] in a Shandon disc electrophoresis apparatus. Gels of 7.5% and 3.75% acrylamide were used in tubes 10.4 cm long by 0.5 cm internal diameter with a current of 8 ma per tube. The current across the gels was stopped when the bromophenol blue front was within 1 cm of the gel end. The dye positions were marked prior to further processing by stabbing Indian ink into the gel with a hypodermic needle. Standards used for calibrating gels were; lysozyme (MW $14.3 \times 10^3$), ovalbumin (MW $45.0 \times 10^3$), trypsinogen (MW $24.0 \times 10^3$), pepsin (MW $34.7 \times 10^3$) and bovine serum albumin (MW $66.0 \times 10^3$). The $R_f$s were recorded both with a densitometer (Helena) and vernier calipers. The gels were stained with Coomassie $$\frac{\text{distance of protein migration}}{\text{distance of dye migration}}$$

B. Iso-Electric focusing

The purified enzymes were concentrated if necessary prior to application onto an Ampholine PAG plate pH 3.5–9.5 (LKB, Stockholm, Sweden). Enzymes were applied approximately 10 to 30 μL onto applicator strips provided by the manufacturers. The plates were run on a Pharmacia FBE 3000 flatbed apparatus with an ISCO 949 power supply. The starting voltage was 450 V with current 25 mA, the voltage rising to 510 V and the current falling to 13 mA at the end of the run. Coloured proteins, such as cytochrome C and haemoglobin were included in each run to visually determine the degree and completion of focussing. Upon completion of the run the pH gradient across the plate was read by means of a surface electrode, and graphed. The gel was fixed for 1 hour in a trichloroacetic acid/sulphosalicylic acid solution followed by destaining for 5 minutes and staining for 10 minutes in Coomassie blue R-250 solution. Final destaining was for 5 hours in an ethanol:acetic acid:water (5:2:13) mixture at 55° C. Asparaginase activity was determined in partially purified enzyme solutions by two methods:
1. Duplicate gels were cut into small pieces. Each piece was macerated for 10 hours after breaking up with a stirring rod in a small volume (1–2 mls) of borate buffer (pH 9.2) prior to running as a normal assay.
2. The location was checked with the agar gel method of Padjack and Padjack [(1972) Analyt. Biochem. 50, 317–320]. This sensitive and convenient method involves overlaying an agar gel included in which is sodium tetraphenylboron (NaB[C$_6$H$_5$]$_4$). This forms a white insoluble complex with NH$_4^+$.

C. Analytical and Preparative Disc Electrophoresis

Polyacrylamide disc electrophoresis was used as an indication of final purity and also as a preparative step but crystallisation was not attempted via this route. The method of Davis [Ann. N.Y. Acad. Sci. (1964) 121, 404–427] was followed. Experiments were performed at pH 9.0 by using separation gels of 4.5 or 7.5% acrylamide for 1 to 2 hours at 2.5 mA per tube. Gels were stained in 1% aqueous Coomassie blue, diluted 1:20 in 12.5% trichloroacetic acid for 1 hour and stored in 10% trichloroacetic acid, after Chrambach et al, [(1967) Analyt. Biochem. 20, 150]. For preparative separations using 0.2 mg of protein per gel, a representative gel was stained for the location of bands, and other gels were examined under ultraviolet light for location of protein bands which were individually removed. The crushed gels were eluted with TRIS/HCl buffer and dialysed to remove gel particles.

Purities of the D-asparaginase at various stages in the isolation procedure shown in the flow diagram are set out in Table 2 below.

TABLE 2

Purification for D-Asparagine (Data combined from 4 runs)

| | Total protein mg | Total Activity units* | Specific Activity units/mg | Relative Purif. | Yield |
|---|---|---|---|---|---|
| 1. High speed supernatant crude extract | 5,000 | 12,000 | 2.4 | — | 100 |
| 2. QAE-A50-Gel Chrom. Step gradient | 450.70 | 6,360 | 14.1 | 5.88 | 53 |
| 3. Hyroxyapatite Step gradient | 105.0 | 4,200 | 40 | 16.67 | 35 |
| 4. G-200 Sephadex Chromatography | 21.2 | 3,600 | 170 | 70.83 | 30 |
| 5. Hydroxyapatite Linear gradient | 10.5 | 2,520 | 240 | 100.00 | 21 |
| 6. QAE-A50 Linear gradient | 6.90 | 1,920 | 280 | 116.67 | 16 |
| 7. Cellulose Acetate Electrophoresis | 3.87 | 1,200 | 310 | 129.17 | 10 |
| 8. Crystallization | 1.89 | 720 | 380 | 153.33 | 6 |

*Activity 1 unit + amount of enzyme giving 1 mMole NH$_4^+$ in 30 minutes under the conditions of the assay.

EXAMPLE 5

METHODS OF ENZYME IMMOBILISATION

A. Covalent Attachment

The asparaginase enzymes were attached to cyanogen bromide activity Sepharose (Pharmacia) by the method of Colowick and Kaplan [1976 Methods in Enymology, Vol. XLIV, Immobilised Enzymes, Ed. by K. Mosbatch, Academic Press, N.Y. ].

B. Ionic Adsorpiton

The same enzymes were adsorbed to Sephadex QAE-A50 (Pharmacia) by the following method:
(a) The enzyme solutions used in the standard assay were concentrated fourfold by passage through a PM-10 Amicon membrane filter.
(b) The concentrated enzyme solutions were added to a quantity of pre-swollen gel, the amount of gel added was 50% in excess of saturation of the gel calculated from the manufacturers data.
(c) The gel was shaken gently for 30 minutes at room temperature then centrifuged at 10,000×g for 10 minutes and resuspended in TRIS/HC1 buffer (pH 8.5). This was repeated twice to remove any non-adsorbed enzyme.
(d) After incubation with substrate a quantity of gel/enzyme was washed with several changes of buffer and reassayed to test continued adsorption of the enzyme.

What we claim is:

1. A D-asparaginase having a molecular weight of about 62,000, an isoelectric point of about 4.8, an optimum pH of about 9.5, no activity agatinst L-asparagine and no activity against L- or D-glutamine.

2. A D-asparaginase as claimed in claim 1, wherein said D-asparaginase is derived from Thermus aquaticus (VARIETY T-351), ATCC number 31,674.

3. An L-asparaginase having a molecular weight of about 80,000, as isoelectric point of about 4.6 an optimum pH of about 9.5, no activity against D-asparagine, and no activity against L- or D-glutamine.

4. An L-asparaginase as claimed in claim 3, wherein said L-asparaginase is derived from Thermus aquaticus (VARIETY T-351), ATCC number 31,674.

5. A process for deriving and separating D-asparaginase having a molecular weight of about 62,000, an isolectric point of about 4.8, an optimum pH of about 9.5, no activity against L-asparagine and no activity against L- or D-glutamine, and L-asparaginase having a molecular weight of about 80,000, an isoelectric point of about 4.6, an optimum pH of about 9.5, no activity against D-asparagine and no activity against L- or D-glutamine, said process comprising the steps of:
(a) providing whole cells of Thermus aquaticus (VARIETY T-351), ATCC number 31,674;
(b) subjecting said whole cells to a cell disrupting process to produce a mixture containing cell debris;
(c) separating an asparaginase-rich fraction from said cell debris in said mixture formed by said cell disrupting process;
(d) concentrating and purifying said asparaginase-rich fraction; and
(e) separating D-asparaginase from L-asparaginase in said asparaginase-rich fraction.

6. A process according to claim 5, and further comprising subjecting D-asparginase separated from L-asparaginase in said asparaginase-rich fraction to purification steps.

7. A process according to claim 5, and further comprising subjecting L-asparaginase from which D-asparaginase has been separated to purification steps.

8. A process according to claim 5, wherein said cell disrupting process comprises subjecting said whole cells to pressure disruption.

9. A process according to claim 5 wherein said cell disrupting process comprises subjecting said whole cells to sonication.

10. A process according to claim 8 or 9, wherein said asparaginase-rich fraction is separated from said cell debris by centrifugation.

11. A process according to claim 10, wherein said centrifugation comprises a first low speed centrifugation to give a supernatant, followed by a second high speed centrifugation of said supernatant obtained from said low speed centrifugation.

12. A process according to claim 5, wherein said steps of concentrating and purifying said asparaginase-rich fraction comprise a series of dialyses and ion exchange processes.

13. A process according to claim 6, wherein said purification steps for purifying said D-asparaginase comprise ultrafiltration and ion exchange.

14. A process according to claim 7 wherein said purification steps for purifying said L-asparaginse comprise ultrafiltration and ion exchange.

15. A process according to claim 6 wherein said purification steps for purifying said D-asparaginase include, as a final purification step, the step of recrystalizing said D-asparaginase.

16. A process according to claim 7 wherein said purification steps for purifying said L-asparaginase include, as a final purification step, the step of recrystalizing said L-asparaginase.

* * * * *